United States Patent
Hurlbut

(10) Patent No.: US 9,311,699 B2
(45) Date of Patent: Apr. 12, 2016

(54) CLEAR MOTTLE ANALYZER FOR MULTILAYER LAMINATES

(75) Inventor: Jeffrey B. Hurlbut, West Springfield, MA (US)

(73) Assignee: Solutia Inc., St. Louis, MO (US)

(*) Notice: Subject to any disclaimer, the term of this patent is extended or adjusted under 35 U.S.C. 154(b) by 359 days.

(21) Appl. No.: 13/306,233

(22) Filed: Nov. 29, 2011

(65) Prior Publication Data

US 2012/0133764 A1 May 31, 2012

Related U.S. Application Data

(60) Provisional application No. 61/418,253, filed on Nov. 30, 2010.

(51) Int. Cl.
*H04N 7/18* (2006.01)
*G06T 7/00* (2006.01)
*G01N 33/38* (2006.01)
*G01N 33/00* (2006.01)

(52) U.S. Cl.
CPC ............. *G06T 7/001* (2013.01); *G01N 33/386* (2013.01); *G01N 2033/0083* (2013.01)

(58) Field of Classification Search
CPC .................. G01N 33/386; G01N 2033/0083; G06T 7/001
USPC .......... 348/127; 382/130, 115, 112, 141, 286; 356/73; 378/62, 22; 364/413
See application file for complete search history.

(56) References Cited

U.S. PATENT DOCUMENTS

| | | | | |
|---|---|---|---|---|
| 4,966,455 A | * | 10/1990 | Avni et al. | 356/73 |
| 5,812,629 A | * | 9/1998 | Clauser | 378/62 |
| 2005/0047643 A1 | * | 3/2005 | Lowe | 382/141 |
| 2007/0036464 A1 | * | 2/2007 | Hill et al. | 382/286 |

* cited by examiner

*Primary Examiner* — Nhon Diep
*Assistant Examiner* — Berteau Joisil

(57) ABSTRACT

This disclosure relates to systems, devices and methods utilized to quantitatively measure the level of mottle in multilayer laminates. The systems and method are generally free of the inconsistencies, variability and inherent biases of the traditional subjective process by which a person of ordinary skill in the art can assess and categorize the mottle of a multilayer laminate. In the method, variations in the images of mottle produced by a shadowgraph are quantified, measured and classified.

18 Claims, 14 Drawing Sheets

PRIOR ART

PRIOR ART

FIG. 14

CLEAR MOTTLE ANALYZER FOR MULTILAYER LAMINATES

CROSS REFERENCE TO RELATED APPLICATION(S)

This Application claims the benefit of U.S. Provisional Patent Application Ser. No. 61/418,253, filed Nov. 30, 2010, the entire disclosure of which is incorporated by reference herein.

BACKGROUND OF THE INVENTION

1. Field of the Invention

This disclosure relates to the field of systems, devices and methods utilized to measure the level of mottle in multilayer laminates.

2. Description of Related Art

Multilayer laminates are generally panels comprised of two sheets of a substrate (such as, but not limited to, glass, polyester, polyacrylate, or polycarbonate) with two or more polymer interlayers sandwiched therebetween. Contemplated polymer interlayers include, but are not limited to, polyvinyl butyral (PVB), polyurethane (PU), poly(ethylene-co-vinyl acetate) (EVA), poly(vinyl)acetal (PVA), polyvinylchloride (PVC), polyethylenes, polyolefins, ethylene acrylate ester copolymers, poly(ethylene-co-butyl acrylate), silicone elastomers, epoxy resins and any acid copolymers and ionomers derived from any of the foregoing possible thermoplastic resins. Multilayer laminates can include multiple layer glass panels and multilayer polymer films. In certain embodiments, the multilayer polymer films in the multilayer laminates may be laminated together. In certain embodiments, these films may have coatings, such as metal, silicone or other applicable coatings known to those of ordinary skill in the art. The individual polymer films which comprise the multilayer polymer films may be laminated together using an adhesive as known to those of ordinary skill in the art.

Generally, multilayer laminates can be produced by the following method. First, one or more polymer interlayers are placed between two substrates to create an assembly. In certain embodiments, the layers could include a multilayer interlayer produced through a coextrusion process. Then, air is removed from the assembly by an applicable process or method known to one of skill in the art; e.g., through nip rollers, a vacuum bag or another deairing mechanism. Following the removal of the air from the assembly, the constituent parts of the assembly are bonded by a lamination process known to one of ordinary skill in the art such as, but not limited to, autoclaving. Amongst other applications, the resultant multilayer laminate glass panels from this process are utilized in architectural window applications and in the windows of motor vehicles and airplanes.

One of the problems in the manufacture of multilayer laminate glass panels is the presence of mottle in the final unitary structure. The term "mottle" refers to an objectionable visual defect in the final unitary structure, namely the appearance of uneven spots. Stated differently, mottle is a measure of the graininess or texture of the surface area of the inner polymer interlayer or polymer interlayers. It is a form of optical distortion.

It is believed that mottle is caused by small scale surface variations of the interfaces between layers of the laminate having different refractive indices. The refractive index of a layer is the measure of the speed of light through that substance. Mottle is theoretically possible with any multiple layer interlayer provided that there is a sufficiently large difference in the refractive index between the layers and there is some degree of interfacial variation.

The presence of mottle in the final unitary structure of a multilayer laminate glass panel can be problematic because a certain degree of optical quality is necessary in many (if not most) of the end-use commercial applications of multilayer laminate glass panels (e.g., vehicular, aeronautical and architectural applications). Thus, both the creation of multilayer laminate glass panels with commercially acceptable levels of mottle and a uniform and systematic method or device that can consistently measure the degree of mottle in a given multilayer laminate glass panel is paramount in the art of multiple layer glass panel manufacturing.

Traditionally, assessments of the degree or amount of mottle in a multilayer glass panel were determined by an inherently subjective process. In this process, mottle was visualized using a shadowgraph-based technique. A shadowgraph is an optical method that reveals non-uniformities in transparent media like air, water, or glass. In principle, the unaided human eye cannot directly see differences or disturbances in transparent air, water or glass. However, all these disturbances/differences refract light rays and, accordingly, they can cast shadows. A shadowgraph exploits this property of the ability of the disturbances or differences in a laminate to cast shadows and utilizes it to project an image of the non-uniformities in the laminate onto a screen.

A shadowgraph is created as follows. A source of light is utilized to provide a uniformly diverging light source. One prerequisite of the light source is that it be a point of light source. If the light source is not a point of light source then inhomogeneities in the light source which could affect the shadowgraph will be projected. In a first step, the multilayer laminate to be tested for mottle is placed somewhere in between the light source and a white background or screen. The light emitted from the light source passes through the multilayer test laminate and is then projected onto the white background or screen to produce the shadowgraph. A diagram illustrating how a shadowgraph is created is depicted in FIG. 1, which depicts a procedure for producing a shadowgraph with a multilayer laminate (specifically with a trilayer laminate).

Generally, as the uniformly diverging light source passes through a multilayer laminate, the direction of the light changes as it passes through layers of different refractive indices as described by Snell's Law. The direction of the light changes according to the ratio of refractive indices and the angle of the incoming light, relative to the plane of the interface. If the interface plane varies due to surface non-uniformities, the angle of the reflected light will vary accordingly. The non-uniformly refracted light leads to an interference pattern resulting in a projected shadowgraph image with light and dark spots.

In the traditional process for ascertaining mottle, the severity of the mottle was assessed and categorized by a side-to-side qualitative comparison of the shadowgraph projections for the multilayer test laminate with a set of standard laminate shadowgraphs representing a series or scale of mottle values ranging from 1 to 4, with 1 representing a standard of low mottle (i.e., a low number of disruptions) and 4 representing a standard of high mottle (i.e., a high number of disruptions), which is optically objectionable. For a better understanding of the traditional process, the pictures of the standard laminate shadowgraphs for the mottle standards 1, 2 and 3 are depicted in FIG. 2. Based upon a visual interpretation of which standard laminate shadowgraph picture the test shadowgraph projection best corresponds with, the test laminate is then placed into the mottle category of the corresponding standard laminate.

A problem in the currently utilized traditional mottle analyzer system is that this process (due to its subjective nature) is inherently susceptible to inconsistencies, person-to-person variation and human bias. Coupled with a recent demand for lower acceptable mottle levels from the commercial sector, this has created a need in the industry for a more quantitative and reproducible test to measure the degree or level of mottle for a multilayer laminate.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of the above described and other problems in the art, described herein, among other things, are tests that are capable of quantitatively determining the mottle value of a given multilayer laminate. The tests present a method generally free of the inconsistencies, variability and inherent biases of the traditional subjective process by which a person of ordinary skill in the art can assess and categorize the mottle of a multilayer laminate. In this method, variations in the images of mottle produced by a shadowgraph will be quantified, measured and classified.

In an embodiment, disclosed herein is a computerized method for quantitatively determining the mottle value of a multilayer laminate, the method comprising: providing a computer having non-transitory computer readable memory; providing a low mottle material and a standard laminate; creating calibration shadowgraphs of the low mottle material and standard laminate; capturing calibration images of the calibration shadowgraphs; storing the calibration images to the memory; providing a multilayer test laminate for which the clear mottle value is to be determined; creating a test shadowgraph of the multilayer test laminate; capturing a test image of the test shadowgraph on a digital camera, the image having pixels; storing the test image to the memory; and comparing the test image to the calibration images using the computer to calculate a mottle value.

In one embodiment, to calculate the mottle value by comparing the test image to the calibration images, the computer: converts the test image into a matrix to obtain the numerical value of the pixels; extracts a slice of the matrix, wherein the slice is the center of the matrix; plots the pixel values of the slice as a function of pixel number to form a profile; and quantifies the mottle value from the profile. The computer may quantify the mottle value by: centering the profile at the y-axis origin; determining the absolute value of the centered profile; calculating the average magnitude in the variation of the pixel level from the absolute value of the centered profile; and computing the mottle value of the multilayer laminate from the average magnitude in the variation of the pixel level.

In another embodiment, the test shadowgraph of the multilayer test laminate is created by: providing a source of light that produces a uniformly diverging light source; providing a surface that is capable of showing a shadowgraph; placing a portion of the multilayer test laminate in between the source of light and the surface; and activating the source of light to project the shadowgraph on the surface. The multilayer test laminate may be placed in a position generally equidistant between the source of light and the surface. In some embodiments, the source of light is a xenon arc lamp. In other embodiment, the surface and multilayer test laminate are oriented parallel to each other. In yet another embodiment, the surface and multilayer test laminate may be oriented at approximately a 22 degree angle relative to the source of light. In still another embodiment, the method further comprises calibrating the computer with the calibration shadowgraphs prior to performing the analyzing step.

In one embodiment, the method further comprises calculating a linear equation via linear regression from the calibration shadowgraphs after the calibrating step.

Also disclosed herein is a clear mottle analyzer device, the device comprising: a surface that is capable of showing a shadowgraph; a source of light; a holder placed between the surface and source of light; a digital camera located perpendicular to the surface; and a system for image capture and data analysis, the system being in communication with the digital camera. In this device, the surface, holder, camera, and source of light are housed within an enclosure with the holder and surface being substantially parallel.

In one embodiment, the system for image capture and data analysis comprises a computer and software. In another embodiment, the surface and holder are oriented at approximately a 22 degree angle relative to the source of light. In other embodiments, the holder can be placed in a position generally equidistant between the source of light and the surface. In yet other embodiments, the source of light may be a xenon arc lamp.

Also disclosed herein is a non-transitory computer readable memory comprising: computer readable instructions for capturing calibration images; computer readable instructions for capturing a test image; computer readable instructions for comparing the test image to the calibration images using the computer to calculate a mottle value. The computer readable instructions for comparing: converts the test image and calibration images into a matrix to obtain the numerical value of the pixels; extracts a slice of the matrix, wherein the slice is the center of the matrix; plots the pixel values of the slice as a function of pixel number to form a profile; and quantifies the mottle value from the profile. In one embodiment, the quantifies comprises: centering the profile at the y-axis origin; determining the absolute value of the centered profile; calculating the average magnitude in the variation of the pixel level from the absolute value of the centered profile; and computing the mottle value of the multilayer laminate from the average magnitude in the variation of the pixel level.

BRIEF DESCRIPTION OF THE DRAWINGS

FIG. 14 provides a screen shot of the results output table in one embodiment.

DETAILED DESCRIPTION OF PREFERRED EMBODIMENTS

Described herein, among other things, are tests that are capable of quantitatively determining the mottle value of a given multilayer laminate by way of a computer and associated software. The tests present a method generally free of the inconsistencies, variability and inherent biases of the traditional subjective process by which a person of ordinary skill in the art can assess and categorize the mottle of a multilayer laminate. In this method, variations in the images of mottle produced by a shadowgraph will be quantified, measured and classified on a computer system and associated software.

Throughout this disclosure, the term "computer" will be used to describe hardware which implements functionality of various systems. The term "computer" is not intended to be limited to any type of computing device but is intended to be inclusive of all machine-based computational devices including, but not limited to, processing devices or processors, personal computers, work stations, servers, clients, portable computers, and hand held computers such as, but not limited to, palmtop devices and Smartphones. Further, each computer discussed herein is necessarily an abstraction of a single machine. It is known to those of ordinary skill in the art that the functionality of any single computer may be spread across a number of individual machines. Therefore, a computer, as used herein, can refer both to a single standalone machine, or to a number of integrated (e.g. networked) machines which work together to perform the actions ascribed to that computer herein or to a system having discrete parts, but which are connected together to operate in conjunction with each other to perform those same actions.

The term "software" as used herein refers to code objects, logic, command structures, or other instructions written in any language and executable in any environment designed to be executed by or on a computer. It should be recognized that software functionality can be hardwired onto a chip or into other hardware while still considering it software within the meaning of this disclosure.

The software will preferably be installed on a hard drive or other memory device or computer readable memory associated with or accessible by the computer so that the software can be executed by the computer via the series of computer readable instructions. It is preferred that the software be operable in a standard operating environment (such as, but not limited to, Windows™, MacOS™, Unix™, or Linux™-based operating systems) and it is more preferred that software allowing communication between user and server computers comprise known Internet operating systems including known server software and client software operating in accordance with known standard. This includes, but is not limited to, Internet browsers utilizing hypertext transfer protocol (http).

Figure 1:
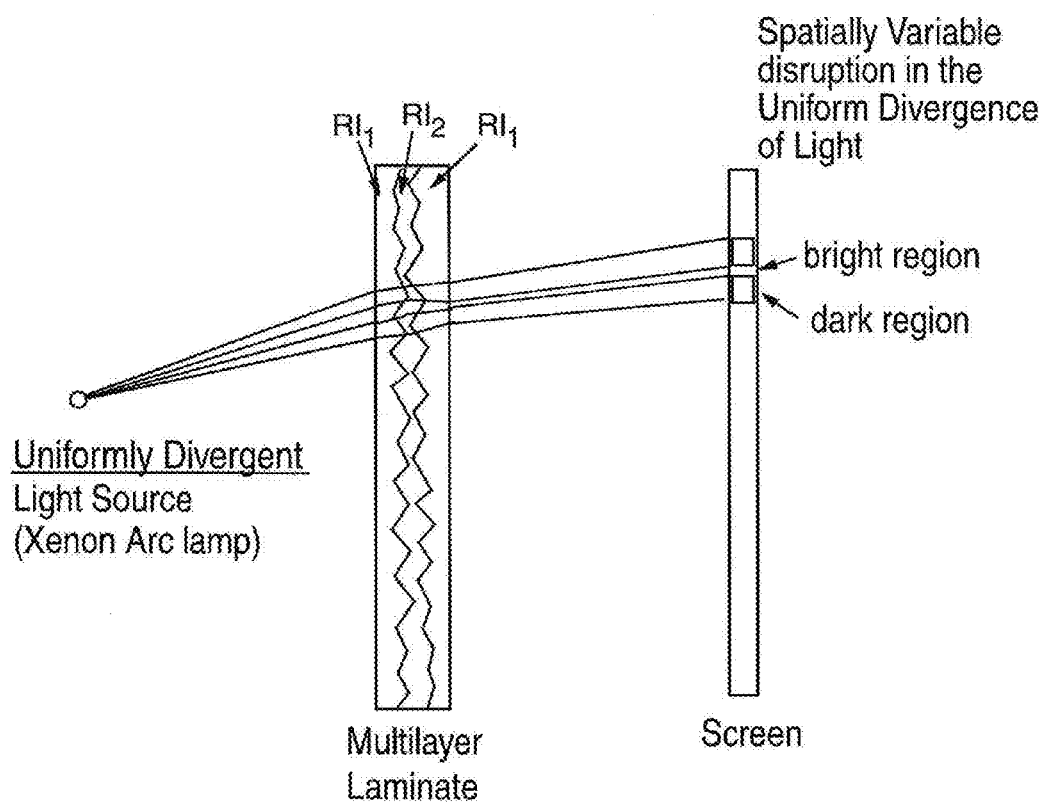
FIG. 1 provides a diagram for the operation of a shadowgraph.
Figure 2:
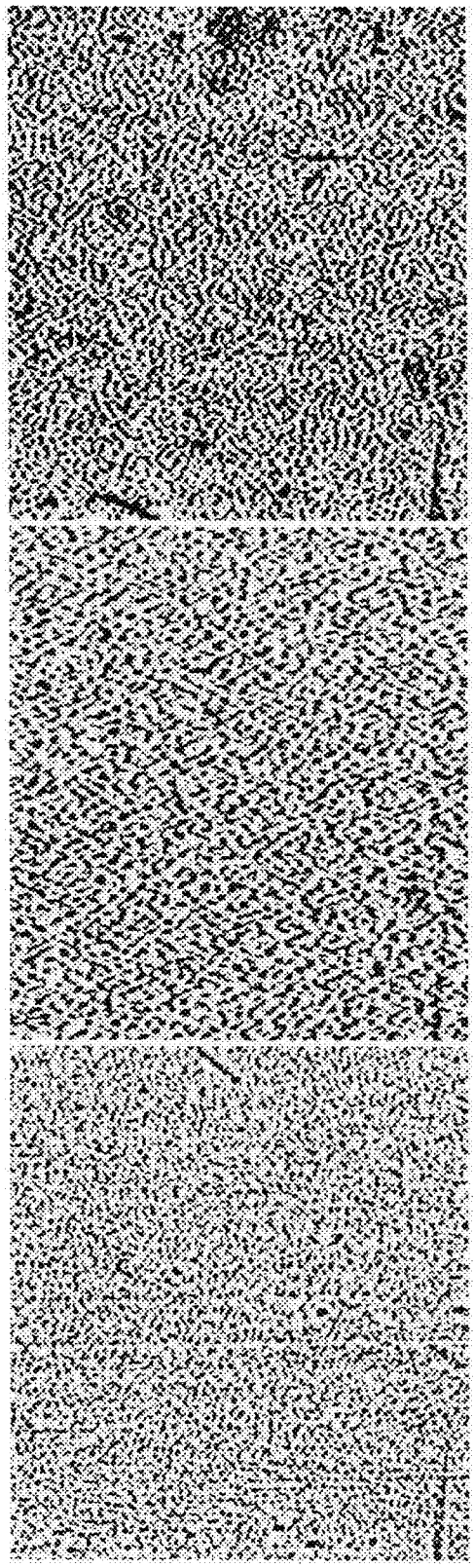
FIG. 2 provides a depiction of the pictures of standard laminate shadowgraphs utilized in the traditional analyzing process for mottle standards 1, 2 and 3.

Turning now to the disclosed method, variations in images of mottle produced from a shadowgraph are quantified to assess and classify the mottle level for a multilayer laminate (referred to herein as multilayer test laminate). In one embodiment of this method, in a first step, a shadowgraph of the multilayer test laminate to be tested is created. Generally, any method known to one of ordinary skill in the art for the creation of a shadowgraph is contemplated in this step of the method. For example, in one embodiment it is contemplated that the shadowgraph is created by placing a portion of the multilayer test laminate to be tested in between a source of light producing a uniformly diverging light source (such as a xenon arc lamp) and a surface that is capable of showing a shadowgraph, such as a white background or a screen as shown in FIG. 1.

Generally, in this first step, shadowgraghs of a blank and standard laminate are also created. The blank shadowgraph, as used herein, is preferably created by utilizing a piece of material with a very low level of mottle (e.g., a piece of glass with no laminate). The standard laminate shadowgraph, as used herein, refers to a laminate with a commercial acceptable (and known) mottle level (i.e., for example, established historically based on the maximum acceptable level of mottle determined from customer feedback). For example, in one embodiment, a standard was developed for a mottle level of about 2.5 ("CMS 2.5").

As discussed more fully below, the blank shadowgraph and standard laminate shadowgraph are used to calibrate the analysis software, and are often referred to herein collectively as calibration shadowgraphs. In this regard, the calibration shadowgraphs generally will not need to be created each time a multilayer test laminate is to be created and analyzed; rather, the calibration shadowgraphs only will be created as needed, i.e., when the system needs to be calibrated as one of ordinary skill in the art would recognize. For example, prior to conducting an initial analysis of a first multilayer test laminate, the system may need to be calibrated. It should be noted that the magnitude of the mottle scale (e.g., CMS 2.5 standard laminate with a scale of 0-4) is otherwise arbitrary, and in practice, any scale could be adopted by using different standards and calibration values.

In one embodiment, the multilayer test laminate will be positioned in a place generally equidistant between the uniformly diverging light source and the surface. However, this positioning of the multilayer test laminate between the light source and the surface is not determinative; any position between the surface and the light source which allows for the creation of a shadowgraph is contemplated. Once positioned, the light emitted from the light source passes through the multilayer test laminate and is projected onto the surface to produce a shadowgraph. It is contemplated, in one embodiment, that the shadowgraphs produced in this first step can produced in the Clear Model Analyzer Device disclosed and described herein by placing the test multilayer laminate in a sample holder that is positioned between a screen and a uniformly diverging light source. The blank and standard laminate also can be positioned and produced in the same manner as described above.

In a second step, the shadowgraph of the projected image(s) is captured with a digital camera, or other comparable technology known to those of skill in the art for capturing an image. In one embodiment, the shadowgraph of the image is captured with a 3.2 Megapixel (Mpx) digital camera such as a FireWire® 3.2 Mpx camera. Again, in one embodiment, this step can be performed in the Clear Mottle Analyzer Device described and disclosed herein. Generally, when performed in the Clear Mottle Analyzer Device, a camera is located generally perpendicular to the reflective screen upon which a shadowgraph is depicted. The reflective screen and sample holder are oriented generally parallel to each other and at about a 22 degree angle from the xenon light source. From this angle, the camera is easily able to capture an image of the shadowgraph(s).

Figure 3:
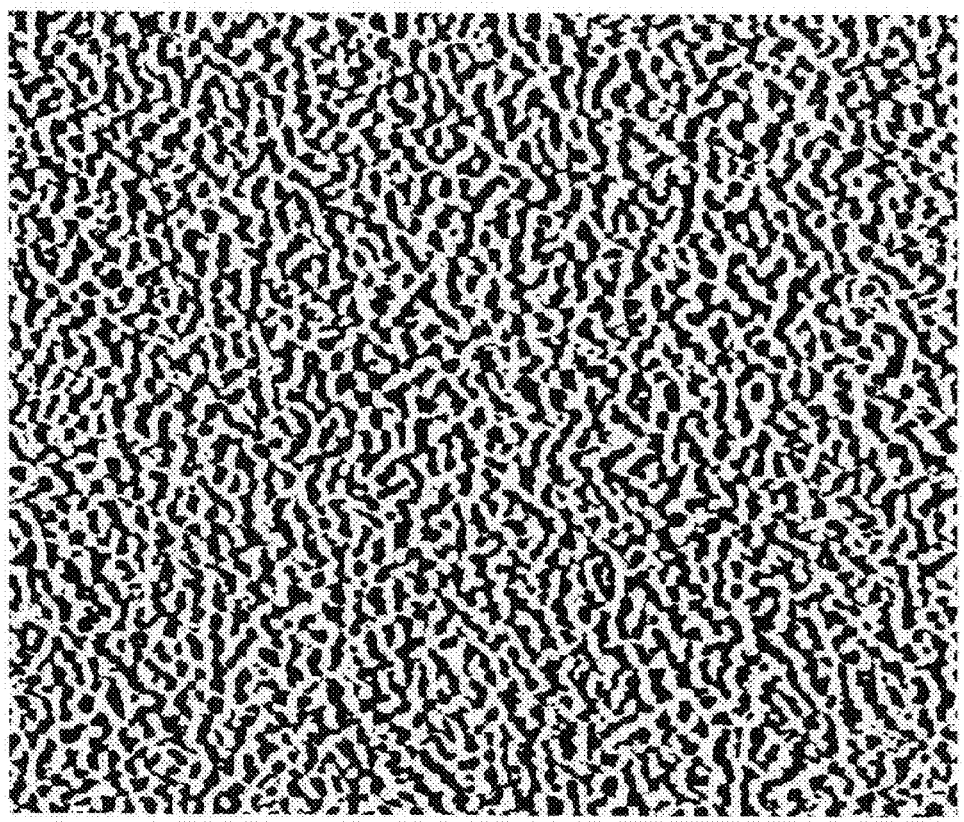
FIG. 3 provides a depiction of a digital image of mottle.

FIG. 3 provides a depiction of a digital image of a shadowgraph showing mottle. The digital image of the shadowgraph captured with the digital camera is generally made up of an array of pixels, each pixel having a value that is, in the simplest case, representative of the grey scale level of the image at that location. Generally, in this second step, images of the calibration shadowgraphs are also captured, if needed. Additionally, after the images are captured, the shadowgraph of the test laminate is projected onto a screen for a user to observe.

Figure 12:
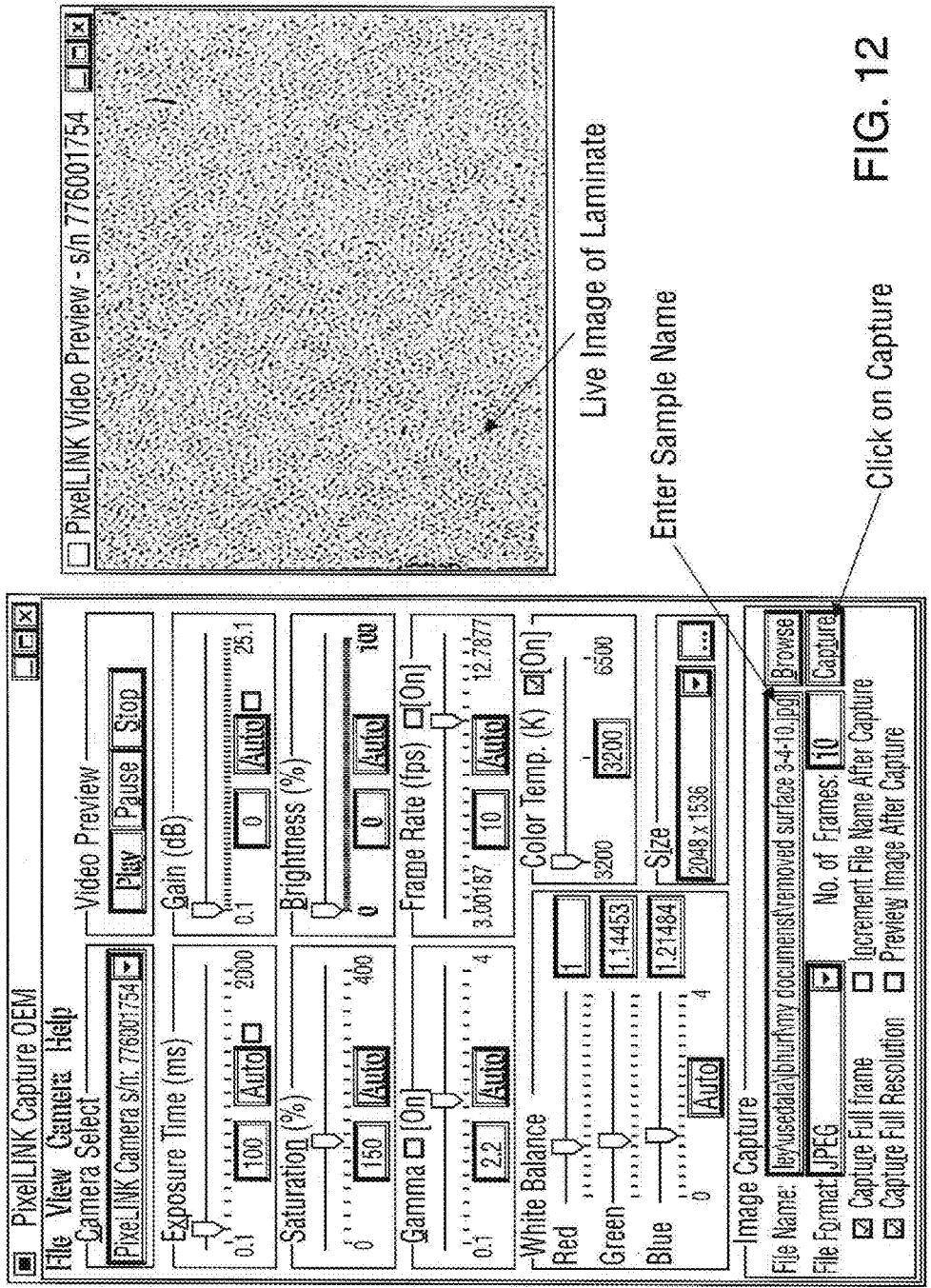
FIG. 12 provides a depiction of the screen shots of the image capture screen for certain embodiments of the software utilized for digital image capture.

Then, in a third step, the user enters the name of the sample (and calibration shadowgraphs, if necessary) into the software for the digital camera utilized and the image of the shadowgraph(s) captured is saved to file. Contemplated software utilized in this step includes, but is not limited to, commercially available data analysis software known to those of skill in the art that allows for additional programming. FIG. 12 provides a depiction of an image capture screen shot and the live viewing screen for certain embodiments of the disclosed method. This process allows for images for all of the laminates, including the calibration standards in a given set of samples to be subsequently captured, labeled and stored.

Once all of the image files have been captured, the image files are then analyzed, such as batch analyzed, by software. In one embodiment, the image files are batch analyzed by the following process. In a calibration screen, the file names for the blank and standard laminate are first entered into the software system. The default mottle values for these standards are CMS 0 (for the blank or low mottle standard) and CMS 2.5 (for the high mottle standard), but can be changed to any value by simply unchecking the default box (as noted above, the magnitude of the mottle scale is otherwise arbitrary and any scale could be adopted). Second, clicking on the "next" button from this calibration screen causes the software program to calculate a linear equation via linear regression that will be used for the subsequent analysis of the test laminates. Third, in a next screen, the file names for all of the image files (up to 10 at a time) to be analyzed are entered. After all the image files to be analyzed are entered, upon selection of the "next" button, the software begins the batch processing of the files to determine the mottle level of each sample and outputs the results into a table.

Figure 13:
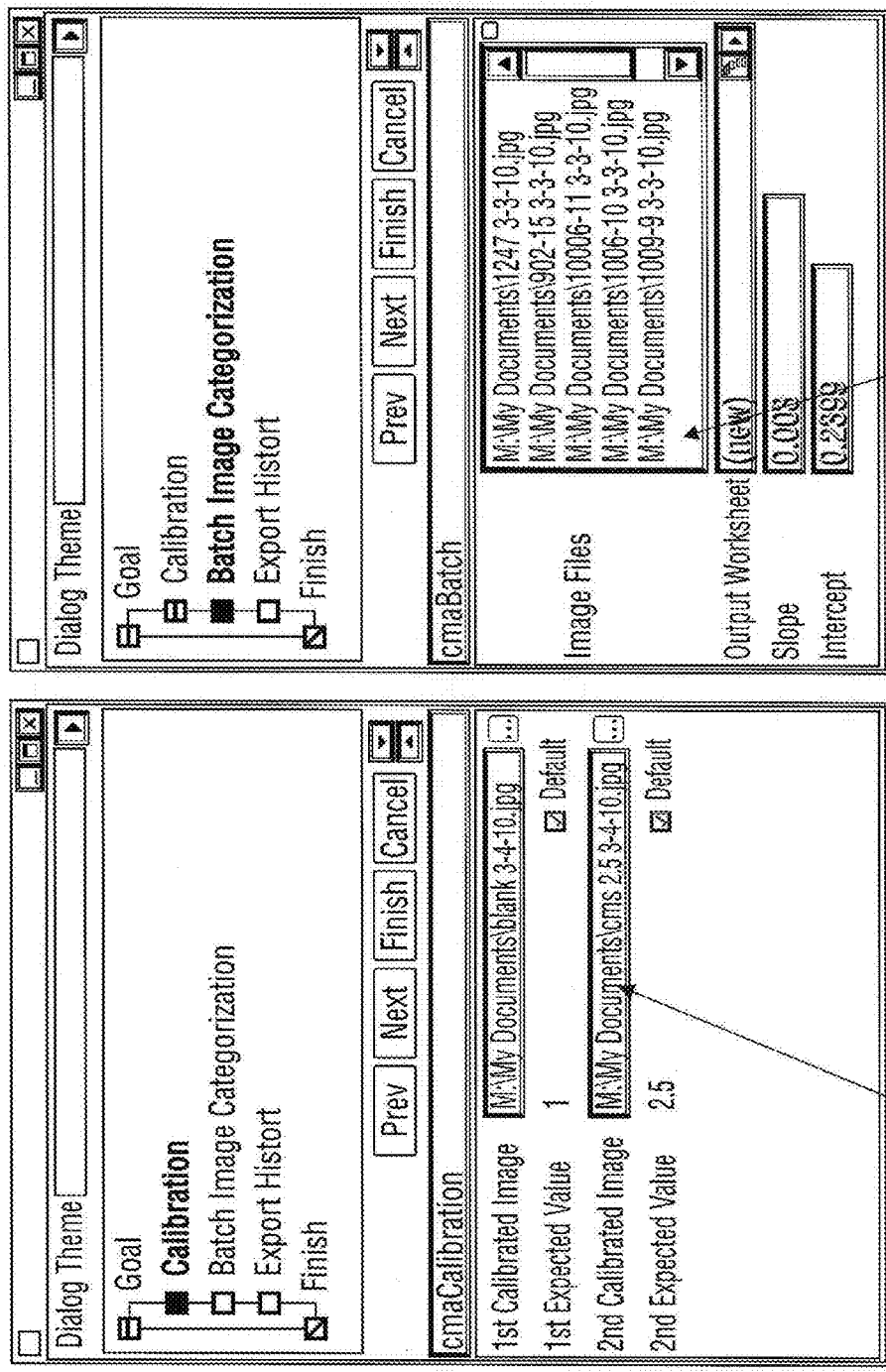
FIG. 13 provides a depiction of the screen shots for the calibration screen (FIG. 13a) and the screen in which the file names of all of the image files to be analyzed are entered (FIG. 13b).
Figure 14:
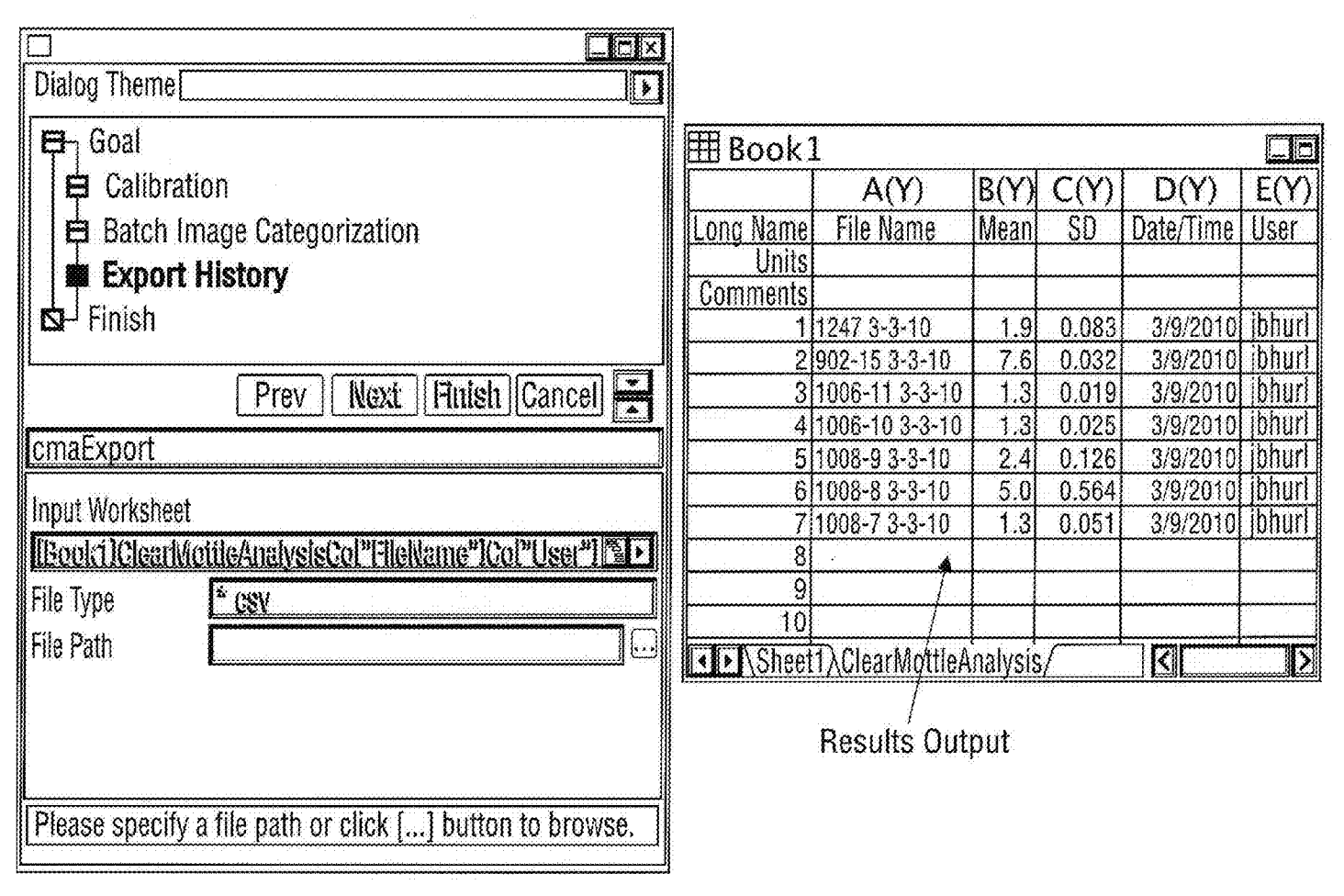

In one embodiment, the output table from the analysis software on the computer includes the laminate image file names, the calculated mean mottle, the standard deviation, the date and the user name. FIG. 13 provides a depiction of the screen shot for the calibration screen in one embodiment (FIG. 13a) and the screen in which the file names of all of the image files to be analyzed are entered (FIG. 13b). FIG. 14 provides a screen shot of the results output table in one embodiment. In general, the mottle calculation is performed on the computer software using the average pixel variation in three (3) adjacent locations on the image centered about the midpoint of the file.

In an embodiment, the analysis and determination of mottle of the samples/images on the software proceeds as follows. The numerical value of each pixel is first obtained by converting the image file into a matrix. It is contemplated that this conversion is accomplished by any image analysis software package that is capable of performing this conversion known to those of ordinary skill in the art that is capable of performing this conversion. In one embodiment, the image analysis software utilized is the Origin® data analysis software produced by OriginLab Corporation but other analysis means or software known now or later developed may be used instead of or in addition to Origin® data analysis software.

Figure 4:
FIG. 4 provides a depiction of the curve created by plotting the pixel values from a digital image of mottle as a function of pixel number.
Figure 5:
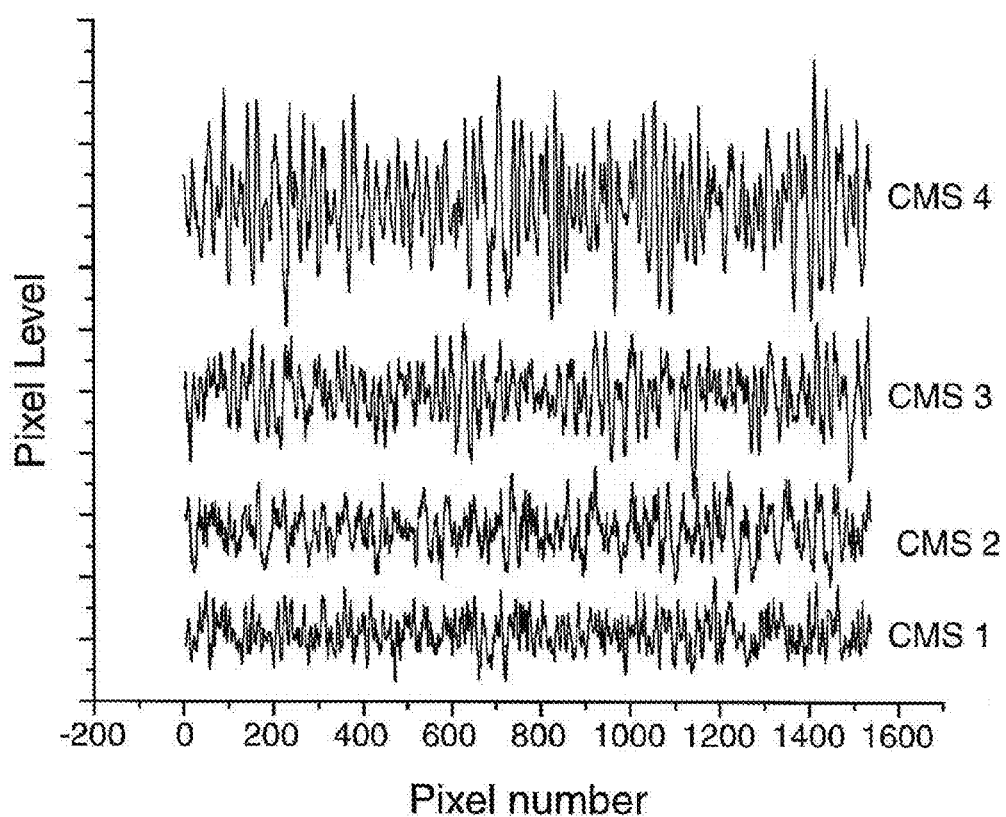
FIG. 5 provides a graphical depiction of the projected mottle interfacial variations for the four different mottle standards.

After converting the image file into a matrix, a slice down the center of the matrix is extracted from the digital image. Then, the pixel values are plotted as a function of pixel number. An example of a curve produced by this plotting is provided in FIG. 4. In general, the variations in the curve represent the transitions in the image from dark to light. For example, FIG. 5 provides a projected mottle variation for the four different mottle standards. As demonstrated in FIG. 5, an increase in the magnitude of the variations can be seen with each increase in mottle level.

Figure 6:
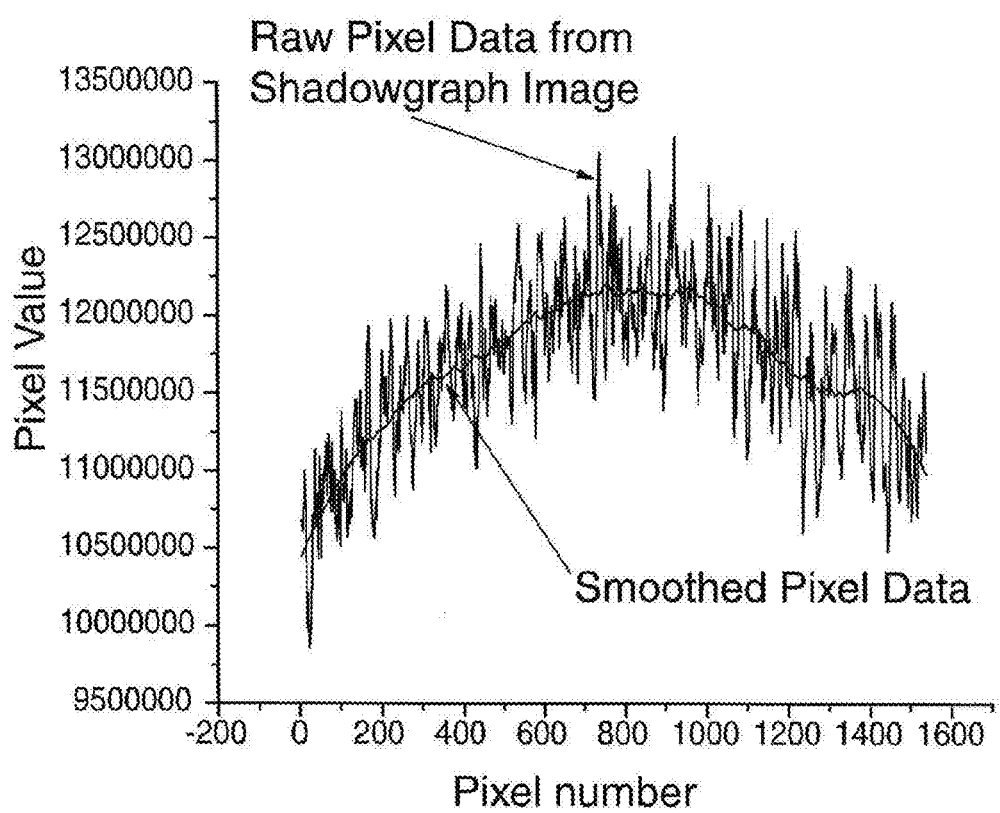
FIG. 6 provides a graphical depiction of the raw pixel data from a shadowgraph image prior to removal of the curvature.
Figure 7:
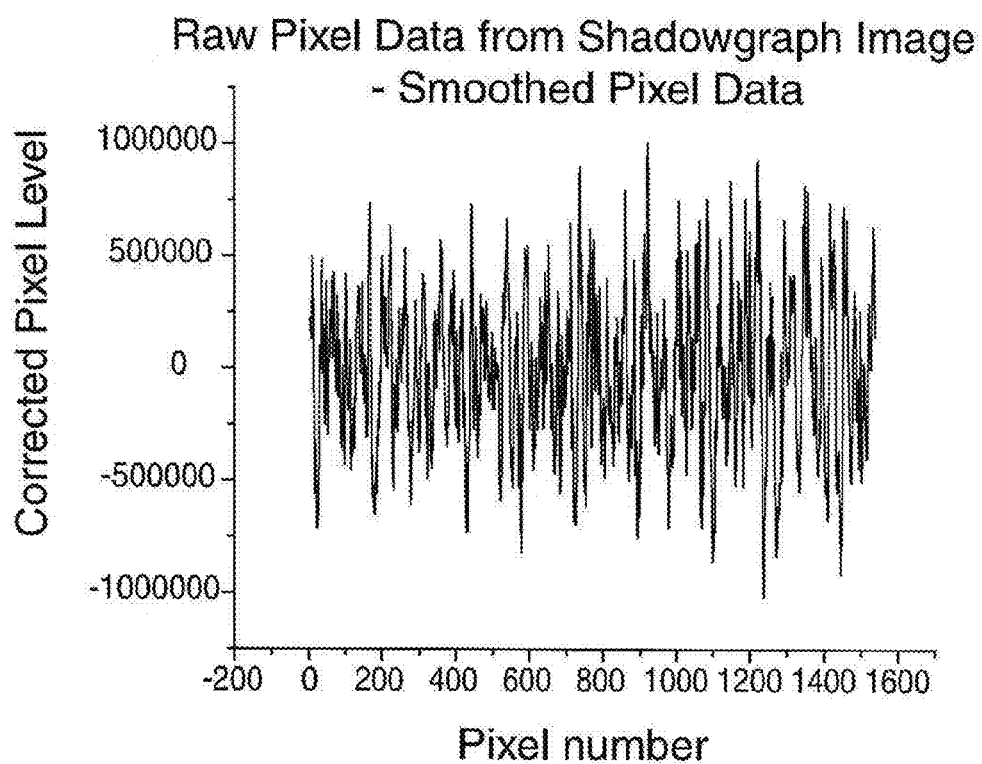
FIG. 7 provides a graphical depiction of the raw pixel data from a shadowgraph image after the S-G curve has been subtracted from the raw pixel curve.
Figure 8:
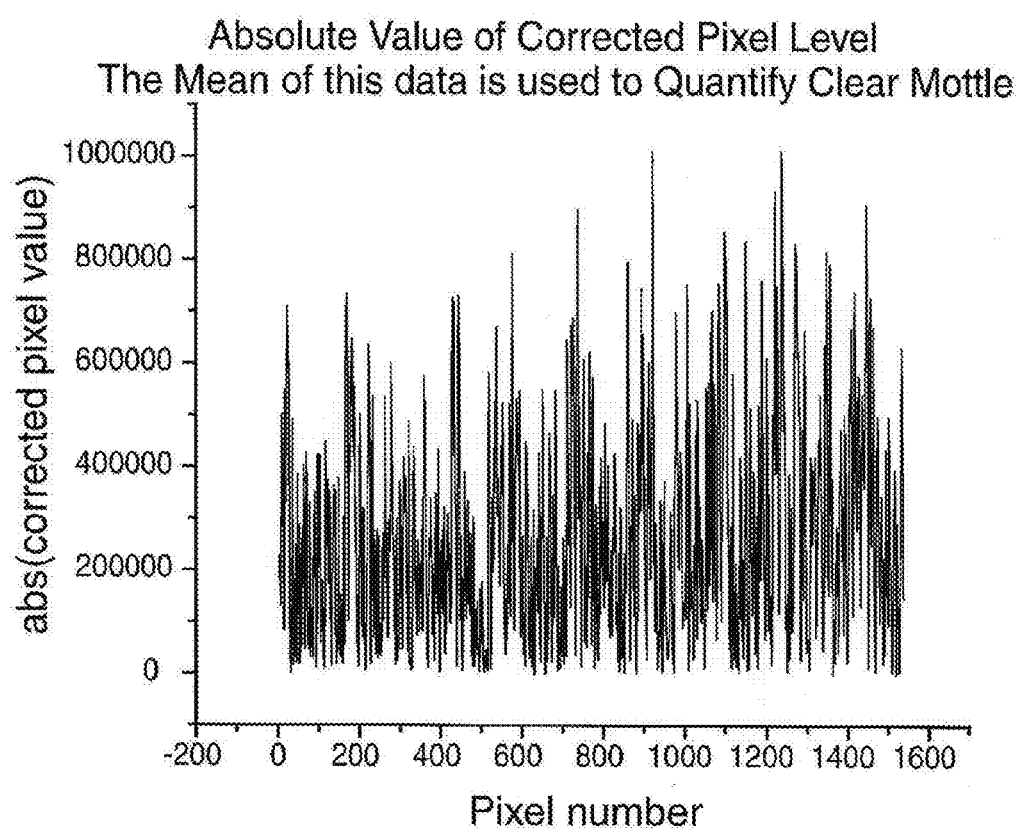
FIG. 8 provides a graphical depiction of the absolute value of a corrected pixel curve.

The magnitudes of the variations in the curve are then utilized to quantify the level of clear mottle. This is accomplished by, first, removing the curvature by any method known to those of skill in the art. In one embodiment, the curvature is removed by generating a smoothed version of the profile using a Savitzky-Golay (S-G) second order polynomial smoothing routine with a suitable high degree of smoothing (around 300 point smoothing). The S-G smoothing routine is a standard smoothing function known to those of ordinary skill in the art. Next, in an embodiment, the S-G curve is subtracted from the original profile to create a new profile without any curvature. This operation centers the curve at about y=0. FIG. 6 provides a graph of the pixel variation (raw data) prior to removal of the curvature. FIG. 7 provides a graph of the smoothed pixel data which results from subtraction of the S-G curve from the raw pixel curve. Since the resulting curve is centered about zero, the absolute value of the curve is taken in order to calculate the average variation in the pixel intensity. The mean absolute value for the resulting curve is then used to determine the average magnitude in the variation of the image. FIG. 8 provides a graph of a curve showing the absolute value of a corrected pixel curve in an embodiment.

Once the average magnitude in the pixel variation is found, this value is can then be utilized in an embodiment to determine the corresponding mottle for the sample using the linear equation developed from the standards. Generally, the higher the level of variation, the higher the corresponding level of mottle.

Figure 9:
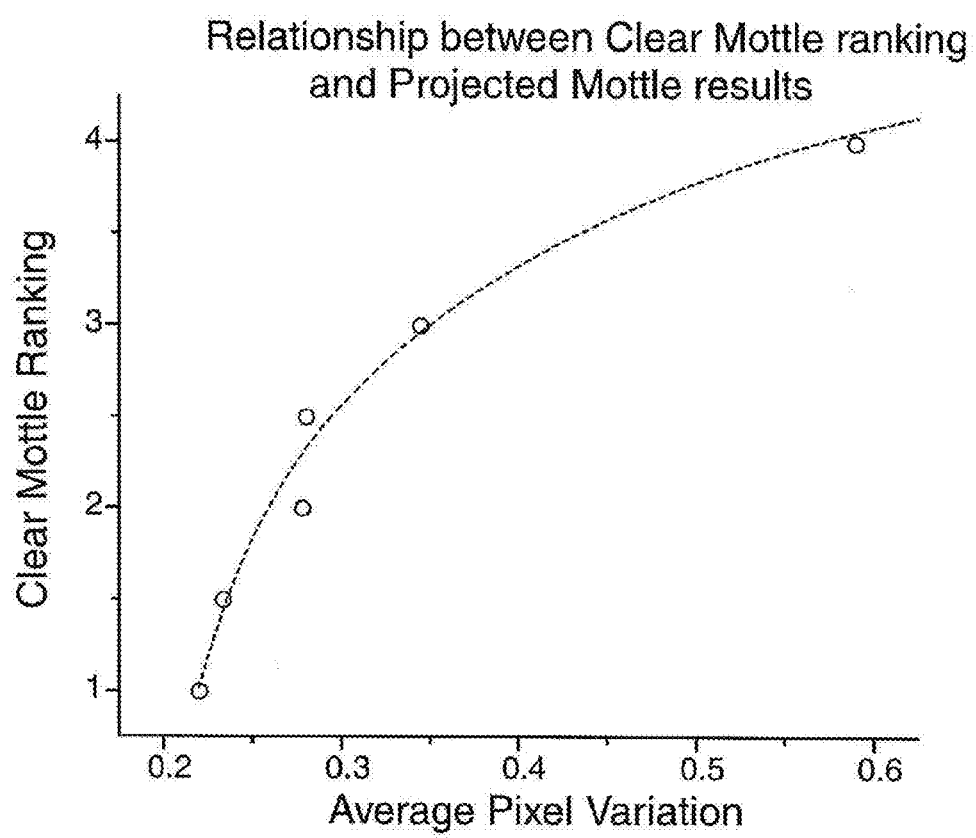
FIG. 9 provides a graphical depiction of average pixel variation plotted versus the standard mottle ranking for the full set of mottle standards.

FIG. 9 provides a graph of average pixel variation plotted versus clear mottle ranking for the full set of clear mottle standards for one embodiment. As demonstrated in the chart in this embodiment, the relationship between the average magnitude in pixel variation and the standard mottle value directly correspond with each other—the higher the level of pixel variation, the higher the level of mottle. Notably, the relationship between the plotted values of FIG. 9 is somewhat linear up to clear mottle values of three (3). After this point, the average pixel variation generally increases more rapidly than the mottle ranking. This is due to the fact that the mottle standards were originally chosen and given values in a somewhat arbitrary manner. The fact that results from the CMA did not match the standards above about 3 says more about the non-linearity of the standards than it does about the instrument. In order to convert the pixel variation values to a clear mottle scale, a simple linear relationship based on the CMS 1 and CMS 2.5 mottle standards rather than a more complex higher order relationship is utilized in one embodiment of the method. Accordingly, a new mottle scale and standard was developed for this embodiment in which a blank image (no laminate) is used to represent zero mottle (mottle=0) and the CMS 2.5 laminate (mottle=2.5) represents the CMS 2.5 laminate as before. This particular method of analysis provides a measurement of mottle relative to a set of standards, wherein any given set of standards could be used in place of the ones discussed. Additionally, in an embodiment, Fourier transform methods can be applied to the pixel variation data to selectively filter out variations of particular spatial frequency or range of frequencies.

Figure 10:
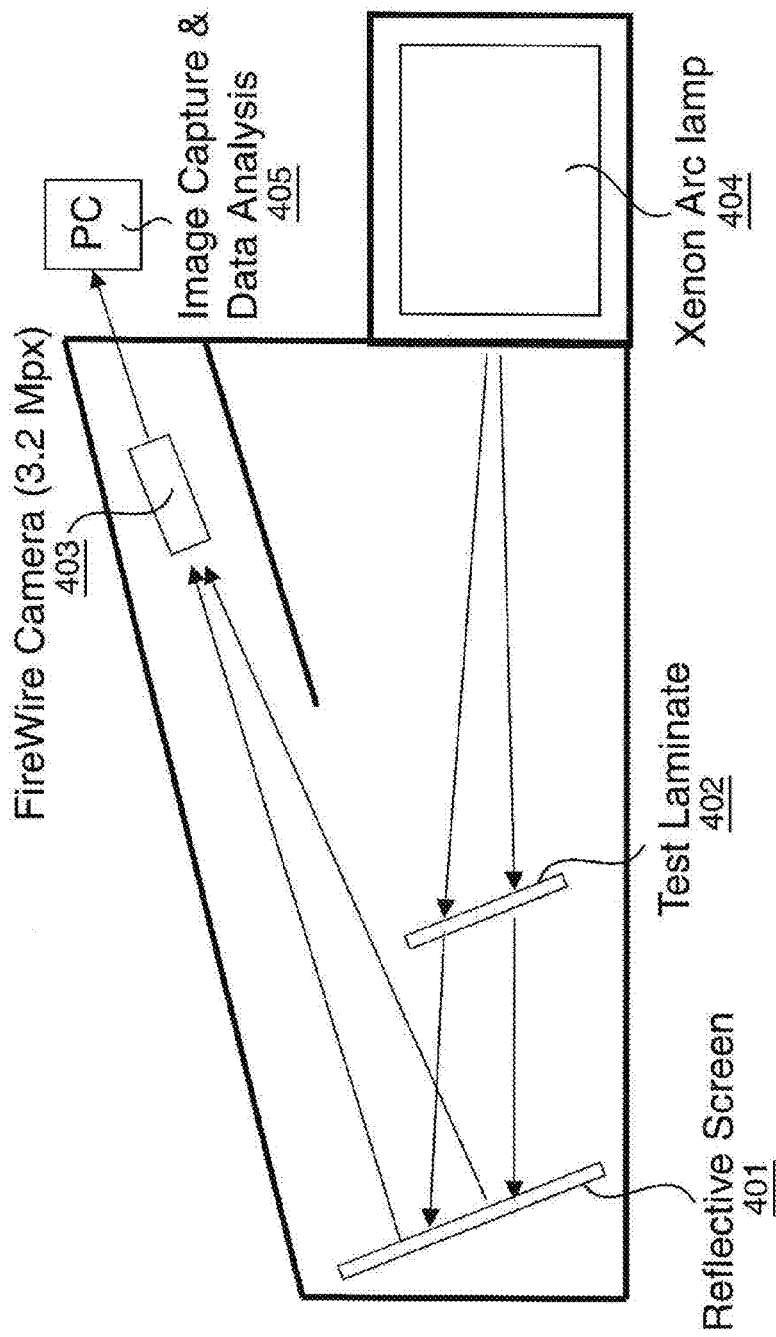
FIG. 10 provides a diagram of the structure of one embodiment of the clear mottle analyzer device.
Figure 11:
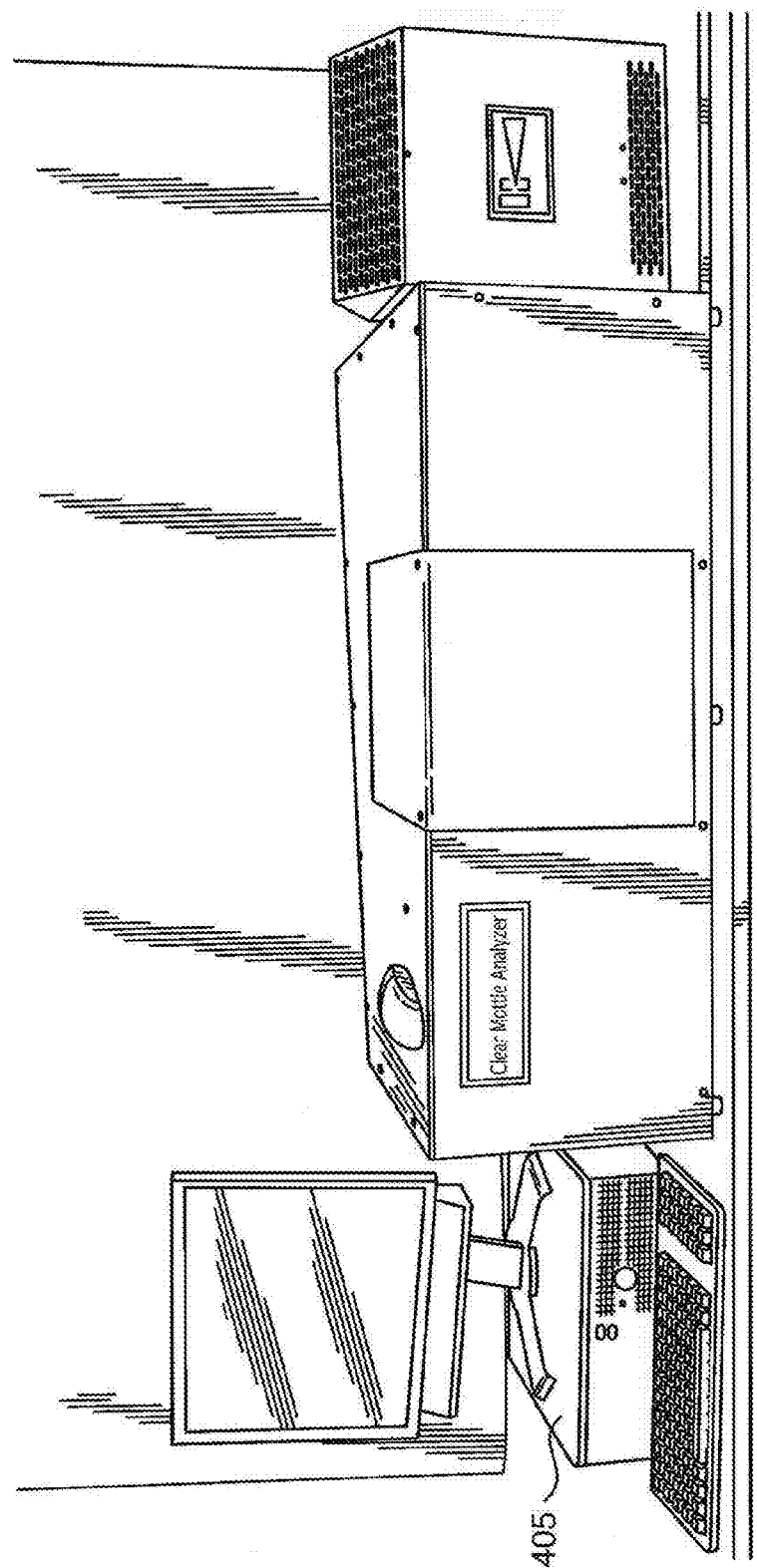
FIG. 11 provides a photograph of the exterior of one embodiment of a clear mottle analyzer device.

Also disclosed herein is a Clear Mottle Analyzer Device. In one embodiment, as depicted in FIG. 10, the Clear Mottle Analyzer Device is comprised of a reflective screen (401), a test laminate holder (402), a digital camera (403) (in one embodiment a FireWire Camera (3.2 Mpx)), a source of light (in one embodiment a xenon arc lamp) (404) and a system for image capture and data analysis (405). The system for image capture and data analysis (405) generally comprises a computer and software able to perform the method and analysis described above (e.g., capturing the images on the computer and analyzing to determine mottle level). In general, these component parts are housed within an enclosure, such as an aluminum enclosure, which is placed upon a base plate, such as an aluminum base plate, with the system for image capture and data analysis (405) in communication with the digital camera (403). In one embodiment, the component parts are oriented within the aluminum enclosure generally in a manner as depicted in FIG. 10. A photograph of the exterior of an embodiment of the Clear Mottle Analyzer Device is provided in FIG. 11. Generally, the Clear Mottle Analyzer Device offers an enclosed space and a device in which the method for quantitatively determining mottle disclosed and described in this application can be performed. As can be seen in the disclosed embodiment, the system (405) and digital camera (403) are in communication by means of a physical, electronic connection. This connection, however, is by no means necessary. As one of ordinary skill in the art would readily appreciate, the system (405) and digital camera (403) could, for example, be in communication wirelessly.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A computerized method for quantitatively determining the mottle value of a transparent multilayer laminate comprising two substrates and at least one polymer interlayer disposed between the substrates, the method comprising:
   providing a computer having non-transitory computer readable memory;
   providing a transparent low mottle material and a transparent standard laminate comprising two substrates and at least one standard polymer interlayer disposed between the substrates, wherein the standard laminate has a known mottle value;
   creating calibration shadowgraphs of the low mottle material and the standard laminate;
   capturing calibration images of the calibration shadowgraphs;
   storing the calibration images to the memory;
   providing a transparent multilayer test laminate for which the clear mottle value is to be determined, wherein the multilayer test laminate comprises two substrates and at least one polymer interlayer disposed between the substrates;
   creating a test shadowgraph of the multilayer test laminate;
   capturing a test image of the test shadowgraph on a digital camera, the image having pixels;
   storing the test image to the memory; and
   comparing the test image to the calibration images using the computer to calculate a mottle value.

2. The method of claim 1, wherein in the comparing, the computer:
   converts the test image into a matrix to obtain the numerical value of the pixels;
   extracts a slice of the matrix, wherein the slice is the center of the matrix;
   plots the pixel values of the slice as a function of pixel number to form a profile; and
   quantifies the mottle value from the profile.

3. The method of claim 2, wherein in the quantifies, the computer:
   centers the profile at the y-axis origin;
   determines the absolute value of the centered profile;
   calculates the average magnitude in the variation of the pixel level from the absolute value of the centered profile; and
   computes the mottle value of the multilayer laminate from the average magnitude in the variation of the pixel level.

4. The method of claim 1, wherein the second creating comprises:
   providing a source of light that produces a uniformly diverging light source;
   providing a surface that is capable of showing a shadowgraph;
   placing a portion of the multilayer test laminate in between the source of light and the surface; and
   activating the source of light to project the shadowgraph on the surface.

5. The method of claim 4, wherein the multilayer test laminate is placed in a position generally equidistant between the source of light and the surface.

6. The method of claim 4, wherein the source of light is a xenon arc lamp.

7. The method of claim 4, wherein the surface and multilayer test laminate are oriented parallel to each other.

8. The method of claim 7, wherein the surface and multilayer test laminate are oriented at approximately a 22 degree angle relative to the source of light.

9. The method of claim 4, wherein the method further comprises calibrating the computer with the calibration shadowgraphs prior to performing the analyzing step.

10. The method of claim 9, wherein the method further comprises calculating a linear equation via linear regression from the calibration shadowgraphs after the calibrating step.

11. A clear mottle analyzer device for quantitatively determining the mottle value of a transparent multilayer laminate, the device comprising:
   a surface that is capable of showing a shadowgraph;
   a source of light, the source being configured to shine light through the multilayer laminate to form the shadowgraph on the surface;
   a holder placed between the surface and the source of light, the holder being configured to hold a transparent multilayer laminate comprising two substrates and at least one polymer interlayer disposed between the substrates;

a digital camera located perpendicular to the surface; and a system for image capture and data analysis, the system being in communication with the digital camera, and being configured for capturing calibration images of calibration shadowgraphs of transparent materials and standard laminates, for capturing a test image of the test shadowgraph of the transparent multilayer laminate, and for comparing the test image to the calibration images to calculate a mottle value for the transparent multilayer laminate;

wherein the surface, holder, camera, and source of light are housed within an enclosure with the holder and surface being substantially parallel to one another.

12. The device of claim 11, wherein the system for image capture and data analysis comprises a computer and software.

13. The device of claim 11, wherein the surface and holder are oriented at approximately a 22 degree angle relative to the source of light.

14. The device of claim 11, wherein the holder is placed in a position generally equidistant between the source of light and the surface.

15. The device of claim 11, wherein the source of light is a xenon arc lamp.

16. A non-transitory computer readable memory for use in a system for quantitatively determining the mottle value of a transparent multilayer laminate, said memory comprising:

computer readable instructions for capturing calibration images of calibration shadowgraphs formed by shining light through transparent materials and standard laminates;

computer readable instructions for capturing a test image of a test shadowgraph formed by shining light through a transparent multilayer laminate that comprises two substrates and at least one polymer interlayer disposed between the substrates;

computer readable instructions for comparing the test image to the calibration images using the computer to calculate a mottle value wherein the computer readable instructions for comparing:

converts the test image and calibration images into a matrix to obtain the numerical value of the pixels;

extracts a slice of the matrix, wherein the slice is the center of the matrix;

plots the pixel values of the slice as a function of pixel number to form a profile; and quantifies the mottle value of the multilayer laminate from the profile.

17. The memory of claim 16 wherein the quantifies comprises:

centering the profile at the y-axis origin;

determining the absolute value of the centered profile;

calculating the average magnitude in the variation of the pixel level from the absolute value of the centered profile; and computing the mottle value of the multilayer laminate from the average magnitude in the variation of the pixel level.

18. The method of claim 1, wherein the polymer interlayer of the multilayer laminate is a multilayer interlayer.

* * * * *